United States Patent [19]

Krishnan et al.

[11] Patent Number: 4,594,375
[45] Date of Patent: Jun. 10, 1986

[54] BIS-(IMIDE-SULFONATE) FLAMEPROOFING AGENTS, THEIR PREPARATION AND THEIR USE FOR FLAMEPROOFING IN POLYCARBONATE

[75] Inventors: Sivaram Krishnan, Pittsburgh, Pa.; Klaus Kircher, Leverkusen; Hans-Jürgen Kress, Krefeld, both of Fed. Rep. of Germany

[73] Assignee: Bayer Aktiengesellschaft, Leverkusen, Fed. Rep. of Germany

[21] Appl. No.: 617,198

[22] Filed: Jun. 4, 1984

[30] Foreign Application Priority Data

Jun. 18, 1983 [DE] Fed. Rep. of Germany ....... 3322057

[51] Int. Cl.$^4$ ............................................. C08K 5/16
[52] U.S. Cl. ...................................... 524/89; 524/94; 524/611; 524/612; 548/433
[58] Field of Search ................... 548/433; 524/89, 94, 524/611, 612

[56] References Cited

U.S. PATENT DOCUMENTS

| | | | |
|---|---|---|---|
| 3,951,910 | 4/1976 | Mark | 260/45.9 |
| 4,039,509 | 8/1977 | Mark | 260/45.8 R |
| 4,185,009 | 1/1980 | Idel et al. | 260/45.9 |
| 4,289,784 | 9/1981 | Bochis et al. | 424/274 |
| 4,320,049 | 3/1982 | Krishnan et al. | 524/94 |

*Primary Examiner*—Lester L. Lee
*Attorney, Agent, or Firm*—Gene Harsh; Joseph C. Gil; Aron Preis

[57] ABSTRACT

The present invention relates to novel bis-(imide-sulphonates) of the formula (I), a process for their preparation, their use for flameproofing aromatic, thermoplastic polycarbonates obtained from halogen-free diphenols, and thermoplastic aromatic polycarbonates obtained from halogen-free diphenols and containing 0.01 to 1% by weight, of bis-(imide-sulphonate) of the formula (I), based on an aromatic, thermoplastic polycarbonate.

9 Claims, No Drawings

BIS-(IMIDE-SULFONATE) FLAMEPROOFING AGENTS, THEIR PREPARATION AND THEIR USE FOR FLAMEPROOFING IN POLYCARBONATE

The present invention relates to bis-(imidesulphonates) of the formula (I)

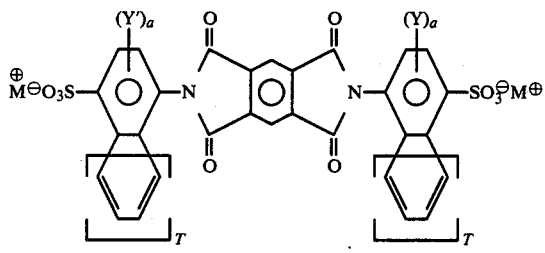

wherein

Y and Y' independently of one another represent a lower alkyl group with 1 to 4 carbon atoms, a represents 0 or an integer from 1 to 4, M represents an alkali metal and T represents 0 or 1.

Suitable alkyl groups are methyl, ethyl, n-propyl, isopropyl, n-butyl and isobutyl groups; suitable alkali metals are sodium and potassium.

The bis-(imide-sulphonates) of the formula (I) are prepared by reacting benzene-1,2,4,5-tetracarboxylic acid anhydrides with the corresponding aminosulphonic acid of the general formula (II) in a molar ratio of 1 to 2 in the presence of sodium carbonate or potassium carbonate, which is used in equivalent amounts, based on the sulphonic acids (II), at temperatures of 130°–150° C., solvents, such as dimethylformamide, also being used. In the sulphonic acids of the formula (II)

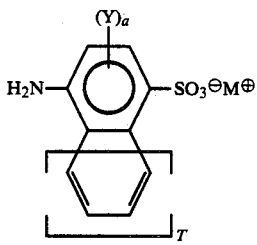

Y, a and T correspond to the meaning given for formula (I).

The present invention thus also relates to a process for the preparation of the bis-(imide-sulphonates) of the formula (I), which is characterised in that benzene-1,2,4,5-tetracarboxylic acid bis-anhydride is reacted with an aminosulphonic acid of the formula (II)

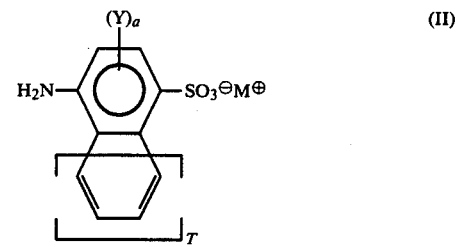

wherein Y, a, M and T have the meaning given for formula (I) in a molar ratio of bis-anhydride to aminosulphonic acid of 1 to 2 at temperatures of 130° C. to 150° C., dimethylformamide also being used, in the presence of equivalent amounts of sodium carbonate or potassium carbonate, based on the particular amount of aminosulphonic acid of the formula (II).

The new bis-(imide-sulphonates) of the formula (I) are suitable for flameproofing aromatic, thermoplastic polycarbonates, these being used in amounts of 0.01 to 1% by weight, based on the weight of the polycarbonate resin, preferably in amounts of 0.1 to 0.75% by weight, based on the weight of the polycarbonate resin.

The present invention thus furthermore relates to the use of the bis-(imide-sulphonates) of the formula (I) for flameproofing aromatic, thermoplastic polycarbonates obtained from halogen-free diphenols.

Flame-retardants for polycarbonates, which correspond to the following formula (III)

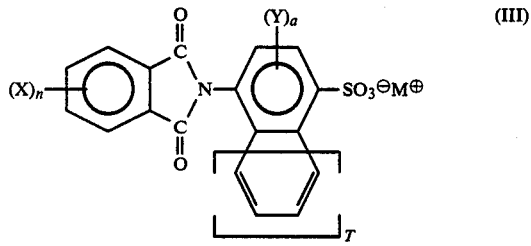

wherein

Y, a, T and M have the meaning given for formula (I), and wherein

X is a halogen and n is an integer from 1 to 4, are known (see European Offenlegungsschrift (European Published Specification) No. 43,997 or U.S. Pat. No. 4,320,049).

Compared with these known flameproofing agents, the bis-(imide-sulphonates) of the formula (I) according to the invention have the effect that, although they carry no halogen at all in the molecule, they exhibit a flameproofing action and thus result in a halogen-free flameproofed polycarbonate with a UL-94-V-0-classification.

The lithium-N-phenyl-phthalimide-4-sulphonate mentioned according to U.S. Pat. No. 3,951,910 and DE-OS (German Published Specification) No. 2,461,144 as a flameproofing agent for polycarbonates effects only SE-II classification in linear bisphenol A polycarbonates, even in amounts of 1 percent by weight.

In addition, the bis-(imide-sulphonates) of the formula (I) are characterised by a low volatility under normal polycarbonate processing conditions.

Aromatic, thermoplastic polycarbonates in the context of the present invention are polycondensates obtainable by reacting halogen-free diphenols, in particular dihydroxydiarylalkanes, with phosgene or diesters of carbonic acid, dihydroxydiarylalkanes in which the aryl radicals carry an alkyl group in the o- and/or m-position relative to the hydroxyl group also being suitable in addition to unsubstituted dihydroxydiarylalkanes. Branched polycarbonates, for example the branched according to U.S. Pat. No. 4,185,009 and German Patent Specification No. 2,500,092, are also suitable.

The aromatic, thermoplastic polycarbonates have mean weight-average molecular weights Mw between 10,000 and 200,000, preferably between 20,000 and 80,000, determined by measurement of the relative viscosity in $CH_2Cl_2$ at 25° C. and a concentration of 0.5 g/100 ml, after appropriate calibration.

Examples of suitable halogen-free diphenols are hydroquinone, resorcinol, 4,4'-dihydroxydiphenyl, bis-(hydroxy-phenyl)-alkanes, such as, for example, $C_1$–$C_8$-alkylene- or $C_2$–$C_8$-alkylidene-bisphenols, bis-(hydroxyphenyl)-cycloalkanes, such as, for example, $C_5$–$C_{15}$-cycloalkylene- or $C_5$–$C_{15}$-cycloalkylidene-bisphenols, and bis-(hydroxy-phenyl)sulphides, ethers, ketones, sulphoxides or sulphones, furthermore, $\alpha,\alpha'$-bis-(hydroxyphenyl)-diisopropylbenzene and the corresponding nuclear-alkylated compounds. Polycarbonates based on 2,2-bis-(4-hydroxy-phenyl)-propane (bisphenol A), 2,2-bis-(4-hydroxy-3,5-dimethyl-phenyl)-propane (tetramethylbisphenol A) or 1,1-bis-(4-hydroxyphenyl)-cyclohexane (bisphenol 2), and those based on trinuclear bisphenols, such as $\alpha,\alpha'$-bis-(4-hydroxyphenyl)-p-diisopropylbenzene, are preferred.

Other halogen-free diphenols which are suitable for the preparation of the polycarbonates are described in U.S. Pat. Nos. 3,028,365 and 3,275,601.

Examples of suitable branching agents are 1,3,5-tri-(4-hydroxyphenyl)-benzene, tri-(4-hydroxyphenyl)-phenylmethane, hexa-(4-hydroxyphenylisopropyl)-phenyl)ortho-terephthalate, tetra-(4-hydroxyphenyl)-methane, 1,4-bis-(4',4''-dihydroxyatriphenyl-methyl)-benzene, trimesic acid, cyanuric chloride and 3,3-bis-(4-hydroxy-3-methyl-phenyl)-2-oxo-2,3-dihydroindole.

Examples of suitable chain stoppers for regulating the molecular weight are, in a known manner, phenol and alkylphenols.

The aromatic, thermoplastic polycarbonates are prepared in a known manner, for example by the phase boundary process or by the homogeneous solution process. The aromatic, thermoplastic polycarbonates can also be prepared by the known transesterification process.

If the bis-(imide-sulphonates) of the formula (I) are used by themselves, preferred polycarbonates in the context of the present invention are branched polycarbonates which are based on bisphenol A and have a branching agent content of 0.3 to 1.0 mol %, per mol of bisphenol A; if other customary flameproofing additives, such as polytetrafluoroethylene polymers, cryolite or $BaCO_3$, are added, linear polycarbonates based on bisphenol A are also preferred polycarbonates.

The new flameproofing agents can be incorporated into the polycarbonates by, for example, mixing and subsequent granulation of the material via a twin-screw extruder at 270°–280° C.

The optimum processing conditions are such that a throughput of 18 kg/hour is achieved at a speed of rotation of 40–80 revolutions/minute.

The twin-screw extruder used is an apparatus from Messrs. "Werner and Pfleiderer" designated ZSK 53.

The present invention thus also relates to a process for flameproofing aromatic, thermoplastic polycarbonates obtained from halogen-free diphenols, which is characterised in that bis-(imide-sulphonates) of the formula (I) are incorporated into aromatic, thermoplastic polycarbonates, which are obtained from halogen-free diphenols, in amounts of 0.01 to 1% by weight, preferably 0.1 to 0.75% by weight, based on the aromatic, thermoplastic polycarbonate, if appropriate in the presence of other additives, via a twin screw extruder, a temperature of 270°–280° C. and a throughput of 18 kg/hour at a speed of rotation of 40–80 revolutions/minute, in particular 60 revolutions minute, being maintained.

The invention furthermore relates to the aromatic, thermoplastic polycarbonates which are obtained from halogen-free diphenols and contain 0.01 to 1% by weight, preferably 0.1 to 0.75% by weight, based on aromatic, thermoplastic polycarbonate, of bis-(imide-sulphonate) of the formula (I).

To the admixtures, according to the invention, of polycarbonate and bis-(imide-sulphonate) of the formula (I) can also additionally contain, in a known manner (see, for example, DE-OS (German Published Specification) No. 2,535,262) polytetrafluoroethylene polymers, it being possible to use polytetrafluoroethylene polymers which either are fibre-forming or are not fibre-forming. The amount of polytetrafluoroethylene polymers to be employed should be between 0.1 and 3% by weight, preferably between 0.01 and 2% by weight, based on the aromatic, thermoplastic polycarbonate.

The admixtures, according to the invention, of polycarbonate and bis-(imide-sulphonate) of the formula (I) can also contain other additives conventional in polycarbonate chemistry, such as, for example, pigments, dyestuffs, fillers, stabilisers or mould release agents.

The admixtures according to the invention can be processed to shaped articles or films.

Shaped articles are produced by the injection-moulding process at a temperature of 300°–310° C.

The admixtures according to the invention can be used, for example, in the electrical field for switchplates, sockets, socket plates, switchboxes and the like, in the domestic sector for housing components for irons and coffee machines and in the industrial apparatus field, for example for computer housing components.

The admixtures, according to the invention, of polycarbonate and bis-(imide-sulphonate) of the formula (I) having a flame-repellency designated V-0 according to the UL-94-V test.

In the UL-94 test (Underwriters' Laboratories Inc.), polycarbonate samples are shaped to bars having the dimensions 127 mm × 12.7 mm × 1.6 (or 3.2) mm (5.00 inches × 0.5 inch × 1/16 (or ⅛) inch). The bars are mounted vertically such that the underside of the test piece is 305 mm above a strip of bandaging material. Each test bar is ignited individually by means of two successive ignition operations of 10 s duration, the burning properties are observed after each igniting operation and the sample is then evaluated. To ignite the sample, a Bunsen burner with a blue flame 10 mm (⅜ inch) high of natural gas with a heat content of $3.73 \times 10^4$ kJ/m³ (1,000 BTU per cubic foot) is used.

The UL 94 V-0 classification involves the properties described below for materials which have been tested in accordance with the UL-94 specification. The polycarbonates in this class contain no samples which burn for longer than 10 s after each action of the test flame; they show no total flaming time of more than 50 s when each sample batch is subjected twice to the action of the flame; they contain no samples which burn completely to the holding clamp attached to the top end of the sample; they contain no samples which ignite, as a result of burning drops or particles, the cottonwool arranged below the sample; they also contain no samples which glow for longer than 30 s after the test flame has been removed.

Other UL 94 classifications designate samples which are less flame-repellent and self-extinguishing and which release flaming drops or particles. These classifications are designated UL 94 V-1 and V-2. The polycarbonates within the range of this invention characteristically show the properties required for a UL 94 V-0 classification.

EXAMPLES

A. Preparation of bis-(imide-sulphonates) of the formula (I)

$A_1$. N,N'-Bis-(4-sodiumsulphonylphenyl)-pyromellitic acid diimide 0.6 mol (103.8 g) of 4-aminobenzenesulphonic acid and 0.3 mol (31.8 g) of sodium carbonate are introduced into 2,500 ml of dimethylformamide. At 128° C., the reaction mixture gives a yellow solution. 0.3 mol (65.4 g) of pyromellitic anhydride and a small amount of dimethylformamide are added to this solution. A yellow precipitate thereby separates out. The reaction mixture is brought to 146° C. for three hours and is then cooled. The light yellow crystals which have precipitated are filtered off with suction and suspended in about 7 liters of hot distilled water. Thereafter, the residual precipitate is filtered off with suction and under a waterpump vacuum dried at 110° C.

Yield: 148 g; sodium content: theoretical: 8.04%, found: 8.0–7.9%.

$A_2$. N,N'-Bis-(4-potassiumsulphonylphenyl)-p-pyromellitic diimide

In deviation from Example $A_1$, potassium carbonate is used here, otherwise the reaction procedure is identical.

B.

$B_1$. A branched polycarbonate based on bisphenol A, 0.5 mol % of 3,3-bis-(4-hydroxy-3-methyl-phenyl)-2-oxo-2,3-dihydroindole, 3.0 mol % of phenol, as the chain stopper, and phosgene and having a solution viscosity of 1.31 (measured in $CH_2Cl_2$ at 25° C. and in a concentration of 0.5 g per 100 ml) was mixed with N,N'-bis-(4-sodiumsulphonylphenyl)-pyromellitic acid diimide ($A_1$), the mixture was extruded and the fire-repellency of the extruded material in a thickness of 3.2 mm ($\frac{1}{8}$") was investigated according to UL-94. Result: UL-94=V-0.

$B_2$–$B_4$

As a modification of Example 1, a linear polycarbonate was used, and other components in addition to $A_1$ were mixed with the polycarbonate and the mixtures were extruded. The fire-repellency of these samples in various wall thicknesses was investigated in accordance with UL-94. Bis-(4-potassiumsulphonylphenyl)-pyromellitic acid diimide ($A_2$) has been used as the effective component in Example 4. The precise composition and the resulting burning data can be found from the following table.

TABLE 1

| | Polycarbonate* % | $A_1$ % | $A_2$ % | Polytetrafluoroethylene** % | Cryolite % | $BaCO_3$ % |
|---|---|---|---|---|---|---|
| Example $B_2$ | 99.35 | 0.5 | — | 0.15 | — | — |
| UL-94   3.2 mm | V-0 | | | | | |
|             1.6 mm | V-0 | | | | | |
| Example $B_3$ | 98.23 | 0.75 | — | 0.15 | 0.37 | 0.5 |
| UL-94   3.2 mm | V-0 | | | | | |
|             1.6 mm | V-0 | | | | | |
|             0.8 mm | V-1 | | | | | |
| Example $B_4$ | 98.23 | — | 0.75 | 0.15 | 0.37 | 0.5 |
| UL-94   3.2 mm | V-0 | | | | | |
|             1.6 mm | V-0 | | | | | |
|             0.8 mm | V-1 | | | | | |

*Linear polycarbonate based on bisphenol A phenol and phosgene with a η rel of 1.29, measured in $CH_2Cl_2$ at 25° C. as 0.5 g per 100 ml
**polytetrafluoroethylene has an average particle size in the range between 500 and 650 μm and a density of 2.17 to 2.19 $g/cm^3$.

We claim:
1. Bis-(imide-sulphonates) of the general formula

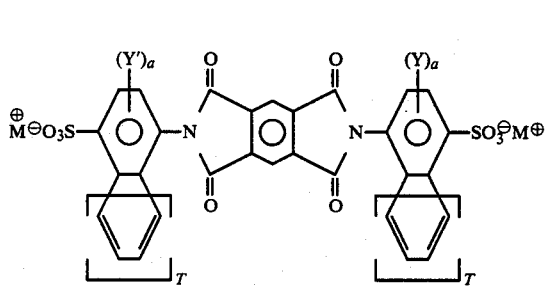

(I)

wherein
Y and Y' independently of one another represent an alkyl radical with 1 to 4 carbon atoms,
a is 0, 1, 2, 3 or 4,
T is 0 or 1 and
M is an alkali metal.
2. A compound according to claim 1 in which M is sodium or potassium.
3. A process for the production of a compound according to claim 1 in which benzene-1,2,4,5-tetracarboxylic acid bis-anhydride is reacted with an aminosulphonic acid of the general formula

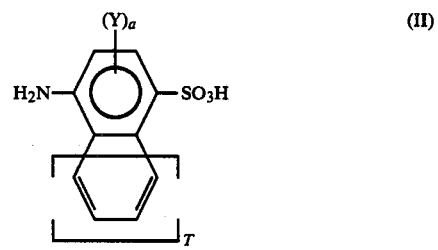

(II)

wherein
Y, a and T have the same meanings as in claim 1, in a molar ratio of bis-anhydride to aminosulphonic acid of 1:2 at a temperature of 130° C. to 150° C., in a solvent in the presence of an equivalent amount of alkali metal carbonate, based on the particular amount of aminosulphonic acid of the formula (II).

4. A process according to claim 3 in which the solvent is dimethylformamide.

5. A process according to claim 3, in which the alkali metal carbonate is sodium carbonate or potassium carbonate.

6. A process of using the bis-(imidesulphonate) of claim 1 for flameproofing an aromatic, thermoplastic polycarbonate obtained from halogen-free diphenols comprising incorporating said bis-(imide-sulphonate) into the aromatic, thermoplastic polycarbonates, in an amount of 0.01 to 1% by weight, based on the aromatic, thermoplastic polycarbonate, via a twin-screw extruder, a temperature of 270°-280° C. and a throughput of 18 kg/hour at a rotation speed of 40-80 revolutions/minute being maintained.

7. A process according to claim 6, in which the incorporation of the bis-(imide-sulphonate) into the polycarbonate is carried out in the presence of another flameproofing additive.

8. A process according to claim 6, in which the bis-(imide-sulphonate) is incorporated in an amount of 0.1 to 0.75% by weight, based on the aromatic, thermoplastic polycarbonate.

9. A thermoplastic composition comprising an aromatic polycarbonate which is obtained from halogen-free diphenols and 0.01 to 1% by weight, based on the aromatic, thermoplastic polycarbonate, of a bis-(imide-sulphonate) according to claim 1.

* * * * *